(12) United States Patent
Bokan et al.

(10) Patent No.: US 10,004,413 B2
(45) Date of Patent: Jun. 26, 2018

(54) SIGNAL ANALYSIS RELATED TO TREATMENT SITES

(71) Applicant: CARDIOINSIGHT TECHNOLOGIES, INC., Independence, OH (US)

(72) Inventors: Ryan Bokan, Cleveland, OH (US); Charulatha Ramanathan, Solon, OH (US); Ping Jia, Solon, OH (US); Maria Strom, Moreland Hills, OH (US)

(73) Assignee: Cardioinsight Technologies, Inc., Independence, OH (US)

( * ) Notice: Subject to any disclaimer, the term of this patent is extended or adjusted under 35 U.S.C. 154(b) by 0 days. days.

(21) Appl. No.: 15/269,396

(22) Filed: Sep. 19, 2016

(65) Prior Publication Data
US 2017/0000364 A1    Jan. 5, 2017

Related U.S. Application Data

(63) Continuation of application No. 14/614,388, filed on Feb. 4, 2015, now Pat. No. 9,445,737.
(Continued)

(51) Int. Cl.
*A61B 5/00* (2006.01)
*A61B 5/04* (2006.01)
(Continued)

(52) U.S. Cl.
CPC .......... *A61B 5/04012* (2013.01); *A61B 5/044* (2013.01); *A61B 5/0422* (2013.01);
(Continued)

(58) Field of Classification Search
CPC ....... A61B 5/044; A61B 5/7425; A61B 5/743; A61B 5/7435; A61B 5/744; A61B 5/748
See application file for complete search history.

(56) References Cited

U.S. PATENT DOCUMENTS

| 6,366,813 B1 | 4/2002 | DiLorenzo |
| 2011/0015496 A1* | 1/2011 | Sherman ............. A61B 5/0006 600/301 |

(Continued)

OTHER PUBLICATIONS

International PCT Application No. PCT/US2015/014519, Filed Feb. 4, 2015, International Search Report and Written Opinion; Authorized Officer: Blaine R. Copenheaver; dated May 14, 2015; Date of Completion: Apr. 10, 2015; 9 pgs.

(Continued)

*Primary Examiner* — Scott Getzow
(74) *Attorney, Agent, or Firm* — Tarolli, Sundheim, Covell & Tummino LLP

(57) ABSTRACT

A method includes storing baseline data representing at least one local or global electrical characteristics for at least a portion of a region of interest (ROI) of a patient's anatomical structure. The baseline data is determined based on electrical measurement data obtained during at least one first measurement interval. The method also includes storing in memory other data representing the at least one local or global electrical characteristics for the at least a portion of the ROI based on electrical measurement data obtained during at least one subsequent measurement interval. The method also includes evaluating the baseline data relative to the other data to determine a change in the at least one local or global electrical characteristics. The method also includes generating an output based on the evaluating to provide an indication of progress or success associated with the applying the treatment.

20 Claims, 6 Drawing Sheets

Related U.S. Application Data

(60) Provisional application No. 61/935,655, filed on Feb. 4, 2014.

(51) Int. Cl.
    *A61B 5/042*      (2006.01)
    *A61B 5/0432*      (2006.01)
    *A61B 5/044*      (2006.01)
    *A61B 5/0452*      (2006.01)
    *A61B 18/06*      (2006.01)
    *A61N 1/362*      (2006.01)
    *A61B 18/00*      (2006.01)

(52) U.S. Cl.
    CPC .......... *A61B 5/0432* (2013.01); *A61B 5/0452* (2013.01); *A61B 5/4839* (2013.01); *A61B 5/4848* (2013.01); *A61B 5/748* (2013.01); *A61B 18/06* (2013.01); *A61N 1/362* (2013.01); *A61B 5/6858* (2013.01); *A61B 5/742* (2013.01); *A61B 2018/00577* (2013.01)

(56) References Cited

U.S. PATENT DOCUMENTS

| | | |
|---|---|---|
| 2011/0028856 A1 | 2/2011 | Zhang |
| 2012/0101398 A1* | 4/2012 | Ramanathan ...... A61B 5/04012 600/523 |
| 2013/0131529 A1 | 5/2013 | Jia et al. |
| 2013/0245473 A1 | 9/2013 | Ramanathan |

OTHER PUBLICATIONS

European Patent Application No. 15746081.7, Filed Feb. 4, 2015, Office Action/Communication dated Aug. 22, 2017, Date of Completion: Aug. 11, 2017; 6 pgs.

* cited by examiner

SIGNAL ANALYSIS RELATED TO TREATMENT SITES

CROSS-REFERENCE TO RELATED APPLICATION

This application is a continuation of U.S. patent application Ser. No. 14/614,388 filed Feb. 4, 2015 (now U.S. Pat. No. 9,445,737), and entitled SIGNAL ANALYSIS RELATED TO TREATMENT SITES, which claims the benefit of U.S. Provisional Patent Application No. 61/935,655, filed Feb. 4, 2014, and entitled ELECTROPHYSIOLOGICAL ABLATION TAGGING. Each of the above-identified applications is incorporated herein by reference in its entirety.

TECHNICAL FIELD

This disclosure relates systems and methods to facilitate signal analysis related to treatment sites.

BACKGROUND

During an electrophysiological (EP) diagnostic procedure (also called EP study), catheters are strategically placed at various locations of the heart to provide signals, which are displayed as traces on a recording system. An EP recording system allows an orderly display of these recordings in the format of individual traces; each trace corresponding to an electrode (catheter electrode/pair or ECG electrode). During the EP study, the electrophysiologist may try to ablate the tissue if the recorded signals indicate abnormal electrical activity.

SUMMARY

Figure 1:
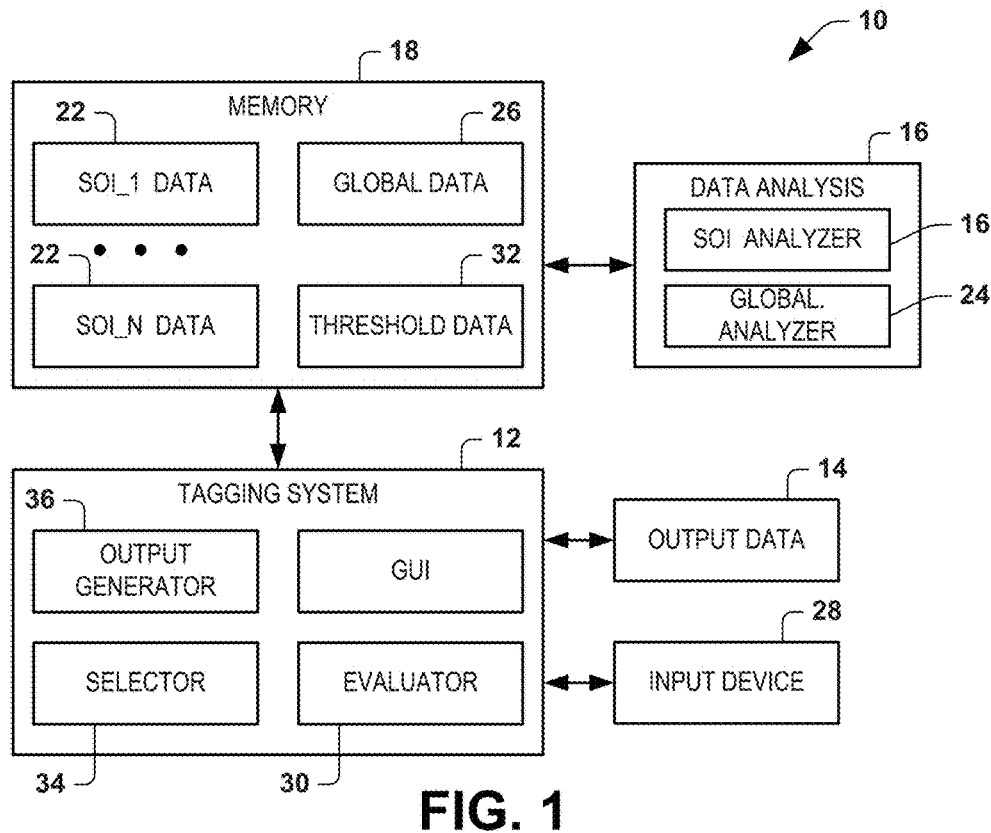
FIG. 1 depicts an example of a block diagram to analyze signals related to treatment sites.

This disclosure relates systems and methods to facilitate signal analysis related to treatment sites.

In one example, the method includes storing in memory baseline data representing at least one local or global electrical characteristics for at least a portion of a region of interest (ROI) of a patient's anatomical structure. The baseline data is determined based on electrical measurement data obtained during at least one first measurement interval prior to applying treatment to the patient. The method also includes storing in memory other data representing the at least one local or global electrical characteristics for the at least a portion of the ROI based on electrical measurement data obtained during at least one subsequent measurement interval that is at least one of during or after applying the treatment. The method also includes evaluating the baseline data relative to the other data to determine a change in the at least one local or global electrical characteristics. The method also includes generating an output based on the evaluating to provide an indication of progress or success associated with the applying the treatment.

In another example, a system includes memory to store baseline data representing at least one local or global electrical characteristics for at least a portion of a region of interest (ROI) of a patient's anatomical structure. The baseline data is determined based on electrical measurement data obtained during at least one first measurement interval prior to applying treatment to the patient. The system also includes machine readable instructions executable by a processor, which include a data analyzer to compute the at least one local or global electrical characteristics for the at least a portion of the ROI based on electrical measurement data obtained during at least one other measurement interval that is different from the at least one first measurement interval. The instructions also include an evaluator to evaluate the baseline data relative to the other data to determine a change in the at least one local or global electrical characteristics. An output generator provides an output based on determined change in the at least one local or global electrical characteristics to provide an indication of progress or success associated with the applying the treatment.

DETAILED DESCRIPTION

This disclosure relates systems and methods to facilitate signal analysis related to treatment sites. The approach disclosed herein can employ calculated parameters, such as based on analysis of an intracardiac signal of interest (SOI) and/or global electroanatomic signals (e.g., from noninvasive signals), to define treatment endpoint for the given SOI. The calculated parameters can be applied to tag treatment sites to provide an indication of the impact of treatment at such sites. In some examples, since mechanisms (e.g., arrhythmia mechanisms and/or an indication of synchrony) can be identified across an anatomic region of interest (e.g., cardiac surface), the approach further provides ability to customize parameter weighting for evaluating SOIs based on mechanisms spatially located in an area that contains the SOIs.

The systems and methods disclosed herein employ intracardiac signals (e.g., measured invasively and/or non-invasively) to ascertain the effect of treatment. For instance, intracardiac signals can be measured directly, such as by utilizing point-by-point or multiple electrode/contact delivery systems. This is in contrast to traditional treatment that is usually performed based on a parameter that relates to the biophysics of the treatment technology itself. For instance, a traditional ablation procedure may be controlled and tagged based on temperature, contact force, impedance, time of delivery, power of energy, etc. of the ablation technology being used. In contrast, the systems and methods disclosed herein use intracardiac signals (e.g., electrograms) themselves, which are believed to provide a more appropriate metric for various forms of treatment, including ablation as well as others disclosed herein.

By way of further example, data representing intracardiac electrical activity associated with a signal of interest (SOI)

measured for a given anatomic site over different time intervals can be stored in memory as SOI data. The SOI data can be analyzed for to ascertain changes in one or more electrophysiological parameters for the given site between the different intervals. The changes can be utilized to determine progress including a treatment endpoint, for example. The SOI data can include and/or be derived from intracardiac signals measured invasively (e.g., from a catheter placed inside or outside the heart), noninvasive electrograms (e.g., reconstructed from sensors placed external to the body surface) or a combination of both. The approach disclosed herein thus can identify such electrophysiological parameters, and combine them with location information, which further can be utilized to provide an electrophysiological visualization means for monitoring status, review and history.

As used herein "distinct arrhythmogenic electrical activity" and variations thereof refer to any one or more detectable conditions in which electrophysiological signals or information derived from such signals exhibits something other than a normal condition, which can be disorganized, irregular, faster or slower than normal, as compared to a baseline for the patient or a corresponding patient population. Examples of arrhythmogenic electrical activity thus can include an arrhythmia for a point or region of an anatomical structure (e.g., heart, brain, etc.), such as can include bradycardia, atrial tachycardia, atrial flutter, atrial fibrillation, atrial-ventricular nodal reentrant tachycardia (AVNRT), atrial-ventricular reciprocating tachycardia (AVRT), ventricular tachycardia, ventricular flutter and ventricular fibrillation. Additionally or alternatively, arrhythmogenic electrical activity also can encompass irregular or dyssynchronous electrical activity across one or more regions, which can include spatial regions within different chambers or different regions within a common chamber.

FIG. 1 depicts an example of a system 10 to facilitate documenting (e.g., tagging) data relating to analysis and/or treatment. As disclosed herein, the system 10 can calculate a change in signal characteristics, such as for a signal of interest (SOI), a zone or other region, and uniquely tag the calculated change to SOI information, to document the impact of treatment at one or more sites as reflected in the calculated change in signal characteristics. As disclosed herein, the calculated change can correspond to a global or regional change in synchrony (e.g., biatrial, biventricular or between other spatial regions of interest), a change in one or more mechanisms of distinct arrhythmogenic electrical activity for one or more zones, and/or a change in local characteristics for a given SOI.

The system 10 includes a tagging system 12 that is programmed to generate output data 14 based upon data analysis 16 performed relative to data 22 and/or 26 stored in memory 18. For example, the tagging system 12 can generate the output data 14 to represent an impact that treatment has on signal characteristics (e.g., locally and/or globally) based on a comparison of baseline data (e.g., measured or derived from measurements prior to applying a given treatment) with respect to corresponding treatment data (e.g., measured or derived from measurements during or after the given treatment has been performed).

The data analysis 16 can include an SOI analyzer 20 program to analyze SOI data 22. The SOI data 22 can include intracardiac signals measured for one or more sites within a region of interest (ROI) of patient's anatomy (e.g., heart, brain or the like). As an example, the SOI analyzer 20 can be programmed to compute one or more signal characteristics based upon intracardiac data obtained for each of the plurality of sites. Examples of the SOI characteristics can include percentage of continuous activation, cycle length characteristics (e.g., cycle length value, cycle length variation), fractionation, deflection slope or the like. The SOI analyzer 20 can also be programmed to compute statistics for one or more of the computed SOI characteristics. The computed characteristics and associated statistics can also be stored in the SOI data 22. The SOI data 22 for each associated SOI, demonstrated as including N SOIs (N being a positive integer), can also include the intracardiac signals analyzed by the SOI analyzer to calculate the SOI parameters as well as SOI metadata. The SOI metadata can include information and characteristics about each SOI, including representing signal changes calculated (e.g., by evaluator 30) from comparing baseline data (tagged as such) and treatment data (tagged to identify a treatment endpoint or an indication of progress during a treatment interval), such as disclosed herein. Thus, the treatment tagging can specify temporal and/or spatial events related to the signals or derived from signal measurements, which can be determined automatically and/or in response to a user input.

The data analysis 16 can also be programmed to include a global analyzer 24 to analyze global data 26 associated with the region of interest. For example, the global data 26 can include or be derived from non-invasive electrical data. As one example, the global data can include electroanatomic data that describes electrical signals and spatial relationships among such signals across the ROI, such as reconstructed electrograms computed for a cardiac envelope. As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the non-invasive sensors have been positioned.

In some examples the ROI for the cardiac envelope can include multiple chambers and even the entire cardiac surface. The global analyzer 24 thus can identify one or more mechanisms of distinct arrhythmogenic electrical activity which can be stored in memory as the global data 26. The arrhythmogenic electrical activity can be global for the ROI (e.g., selected automatically or in response to a user input) or it may include or otherwise specify one or more distinct arrhythmogenic electrical activities for a zone or region according to the selected ROI (e.g., a region or cardiac envelope) based on non-invasive electrical data acquired over one or more time intervals.

Examples of global characteristics stored as the global data 26, which represent one or more mechanisms of distinct arrhythmogenic electrical activity, can include an indication of synchrony (e.g., or dyssynchrony) for the ROI or subregions thereof, such as biatrial synchrony, biventricular synchrony or other multi-chamber synchrony and for different regions within a given chamber (e.g., intra-chamber dyssynchrony). Additionally or alternatively, the global characteristics stored as the global data 26 can include one or more arrhythmia mechanisms, such as rotors and rotor statistics for one or more zones, focal drivers and focal statistics for one or more zones, and fast cycle length across the ROI for one or more zones based on non-invasively acquired electrical data.

The tagging system 12 can be configured to tag various data to indicate the onset of treatment such that selected SOI data and global data 26 can correspond to electrical characteristics associated with the ROI at the onset of treatment such as to define baseline data that is appropriately tagged with metadata in the memory (e.g., to indicate a time when treatment begins or prior thereto). The onset of treatment can be detected in response to an input from an input device 28 (e.g., automatically from a treatment control system or manually in response to a user input indicating application of treatment). The tagging system 12 can also tag data acquired associated with the treatment with metadata defining it as intra-treatment data, for example.

The tagging system 12 can include an evaluator 30 to compare the pre-treatment data relative to corresponding data that is stored in the memory 18, which can include data stored during treatment, after treatment has been performed or both. The evaluator 30 can selectively access portions of the SOI data 22 and/or the global data 26 to ascertain an impact of treatment with respect to the selected data based on real-time data being acquired during the procedure. For example, the evaluator 30 can be programmed to compute a change in one or more local characteristics stored in the SOI data 22 based on intracardiac signals at or near the location where treatment is being applied. For example, the memory 18 can store location data such as from a navigation system (e.g., corresponding to an input device 28) and evaluate SOI data acquired for such location over time. In response to detecting a change in the one or more SOI characteristics, the evaluator 30 can compare the change relative to a corresponding threshold stored as threshold data 32 in memory 18.

As an example, the threshold data 32 can store a plurality of different thresholds for different SOI characteristics which can be selected by a selector function 44 of the tagging system 12. For example, the selector 34 can select a threshold for evaluating one or more SOI characteristics as a function of the global data 26 such as based on one or more arrhythmia mechanisms that have been identified as residing within a zone (e.g., spatial and/or temporal) in which the site associated with the SOI resides. That is, each SOI can include a spatial location in a three-dimensional coordinate system, which can be utilized to determine a zone that contains the SOI, which zone and arrhythmia mechanisms for such zones can be utilized by the selectors 34 to select a one or more corresponding threshold from the threshold data 32. In response to the comparison between the change and the SOI characteristic with respect to the selected threshold, the evaluator 30 can determine an impact of the treatment on the one or more SOI characteristics. In other examples, the evaluator can ascertain an impact of the treatment by calculating a percentage change between the baseline data and one or more SOI characteristics stored as current treatment data.

An output generator 36 can provide an output data 14 to present the results of the evaluation (e.g., an indication of the change of the SOI characteristics) as well as include an indication of the pre-treatment characteristics and the current updated live characteristics based upon current measurements. The pretreatment SOI for a given site can also be provided in the output data 14 along with the current value for the SOI for a corresponding measurement interval. Thus the output data 14 can concurrently display graphically both the pretreatment and current SOIs to enable users to visually identify changes between the pre- and treatment (intra- and/or post-) measurement intervals as well as include output data representing the change in one or more SOI characteristics that have been computed by the SOI analyzer 20 at different measurement intervals (e.g., the pre-treatment interval and a current measurement interval or a post-treatment interval). In some examples, different colors or other visual or text based indicators can be presented based on the output data 14. For example, the output generator 36 can be configured to employ graphical elements with different color scales or other graphical means to differentiate impact at different treatment sites relative to other parts of the graphical map containing a depiction of the 3D map of the heart (see, e.g., FIG. 7).

The output data can also provide an interactive graphical map to dynamically present information in response to a user input activating a GUI element for a given treatment site. In response to activate a GUI element (e.g., 270 or 272 of FIG. 7), for example, the output generator can generate an output based on the baseline data and the treatment data to represent the electrical activity measured for each of the baseline and the treatment measurement intervals, such that the display provides the user an indication of the electrical activity associated with conditions of the region as recorded during each of baseline and the treatment measurement intervals. Additionally, the output generator can provide other visualizations that represent (e.g., on a display) local physiological changes that result as an impact of treatment (e.g., ablation) based on the evaluator 30 detecting changes in measured or computed electrical parameters, such as including one or more of signal amplitude, signal frequency, cycle length and/or fractionation of the SOI.

Additionally or alternatively, as mentioned, the output generator can also provide output data to indicate changes detected in distinct arrhythmogenic electrical activity, which are determined by the global analyzer 24 based on non-invasive data obtained during each of baseline and the treatment measurement intervals. In this way, the effect of treatment locally at a given site on the anatomic region of interest (e.g., endocardially or epicardially), such as ablation, pacing or the like, can be monitored based on global data (e.g., inter-chamber synchrony, intra chamber synchrony, arrhythmia mechanisms in a zone or region). This can further be combined with local SOI characteristics determined by the SOI analyzer, as disclosed herein.

Figure 2:
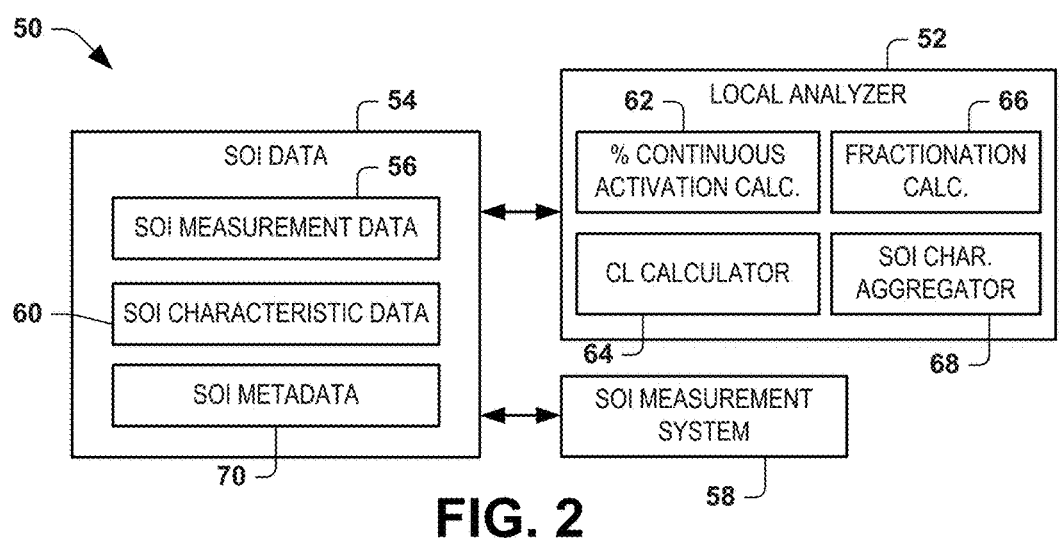
FIG. 2 depicts an example of a block diagram to implement signal analysis for respective signals of interest.

FIG. 2 depicts an example of an SOI analysis subsystem (e.g., corresponding to SOI analyzer 20 of FIG. 1) 50 that processes intracardiac electrical signals (SOI measurement data 54) to determine intracardiac signal characteristics (e.g., calculated parameters derived from intracardiac signals). While in some examples, the SOI measurement data 54 can be based on invasively obtained measurements, the system 50 does not require any particular source of information. For instance, in other examples, the SOI measurement data may be derived by applying a transform to convert reconstructed electrical signals to surrogate estimates of directly measured signals (e.g., transform derived from correlation of invasive and non-invasive measurements, as mentioned above). Stated differently, the system 50 processes the data 54 stored in memory (e.g., stored in memory 18) and does not require any treatment or interaction with a patient to perform the functions and methods disclosed herein. Thus, the system 50 can be implemented as machine readable instructions stored in memory, which instructions and associated data can be accessed and executed by one or more processing units.

The system 50 can also include an intracardiac SOI analyzer (e.g., corresponding to the analyzer 20 of FIG. 1) 52 to analyze SOI measurement data 54 which can be stored in memory. For example, the SOI measurement data 54 can be acquired for one or more anatomic sites during a measurement interval based upon electrical signals measured directly from one or more sensors such as on a probe, catheter or other measurement device. The SOI measurement data 54 can also include site location information for each SOI, which specifies an indication of the location for each of the sites at which the electrical activity was measured, which can be co-registered with a coordinate system (e.g., a 3D coordinate system of patient anatomy). The site location information, for example, can be tracked and provided by a navigation system, and stored as part of the SOI data.

As one example, a probe catheter or other device can be positioned within a patient's body to measure electrical activity at a plurality of sites. As one example, each of the sites can correspond to spatial positions within one or more zones that have been identified (e.g., as determined by the global analyzer 24). In some examples, the site location information can be utilized to provide a graphical representation for the location of the device being used to obtain the measurements that are stored as the SOI measurement data 54 to facilitate localization of the measurement device to a desired measurement site. Once the device is positioned at an SOI, measurement data and associated location information for the SOI can be recorded and stored in the memory as the SOI measurement data 56 for a plurality of sites within the given zone. This measurement process can be repeated for any number of sites (e.g., four or more sites).

The SOI signal characteristic data 60 can be computed by a plurality of signal characteristic calculators. In the example of FIG. 2, the calculators implemented by the local analyzer 52 include a percentage of continuous activation calculator 62, a cycle length characteristic calculator 64, a fractionation calculator 66, and an SOI characteristic aggregator function 68. Each of the calculations 62-68 can compute corresponding statistics for each of the sites that can be stored collectively as SOI characteristic data 60.

As a further example, the percentage continuous activation calculator 62 can compute a percentage of continuous activation for each of the plurality of sites within the given zone. The percentage of continuous activation can be computed by calculating activation time based upon the measured electro activity such as activation corresponding to the derivative of the measured signal, signal peaks in the bipolar electrogram (determined via frequency or peak amplitude analysis as examples) (e.g., dv/dt). The percentage of the measurement time interval during which activation occurs (e.g., activation zones), can be stored as the percentage of continuous activation.

As an example, the percentage continuous activation calculator 62 identifies the active interval around each local activation detection. Based upon frequency and amplitude thresholding criteria, an active zone is defined as the zone surrounding an activated peak which meets the frequency and amplitude thresholding criteria. This segment of signal is the active portion. The percentage of continuous activation is the ratio of active portion to passive portion (e.g., the remaining signal). The percentage of continuous activation can be averaged over each of the cycles in the intracardiac measurement interval.

The cycle length calculator 64 can leverage the activation time that is computed by the calculator 62. For instance, each of the activation times determined over the measurement interval at a given measurement site can be evaluated to compute cycle length (e.g., cycle length determined as a time difference between activation times between consecutive beats). An average cycle length over the measurement interval thus can be calculated by averaging the cycle length values over such interval. The cycle length calculator 64 can also compute an indication of cycle length variation, such as corresponding to a standard deviation or standard error of the cycle length that was computed. Thus, the cycle length calculator 64 can compute multiple CL characteristics, including a mean cycle length and a cycle length variation, which can be stored in the SOI characteristics data 60 as cycle length characteristics for each measurement site.

The fractionation calculator 66 can compute an indication of fractionation for each of the electrograms provided in the electrogram electrical data over a measurement interval. The fractionation can correspond to an average fractionation detected among corresponding beats that have been identified during the measurement interval for each of the plurality of sites. For example, the fractionation calculator can perform a signal analysis on the corresponding electrogram for the measurement interval to detect a frequency of instances of alternating increasing and decreasing potential in the measured SOI. For example, the fractionation calculator can take the time derivative (dv/dt) for the SOI to detect changes in slope (e.g., between positive and negative values) in the signals during the measurement interval. The amount of fractionation during the measurement interval can be normalized and stored as a fractionation value (e.g., a fractionation index) in the SOI characteristic data 60.

The intracardiac characteristic aggregator 68 can aggregate the computed intracardiac characteristics (e.g., cycle length, cycle length variation, percentage continuous activation, fractionation, slope steepness) within a given zone such as by averaging the computed characteristics for sites within a given zone over time to provide an average value of the intracardiac characteristics for each respective zone. The aggregate characteristics for each zone can also be stored as part of the SOI characteristic data 60.

The local analyzer 52 can also generate SOI metadata 70 to describe tagging information that can be added to the SOI data 54 record for a given site associated with the SOI. For example, the metadata 70 can include location data (e.g., from a navigation system) for spatial coordinates of the SOI, temporal information for the data (e.g., time stamps or other indicators). The temporal information can also include an identifier to specify a phase of treatment to which the data belongs (e.g., specifying it as baseline data, intra treatment data, post treatment data, or the like). The metadata 70 can also include an indication of changes in the SOI characteristics calculated by comparing baseline data and current (intra- or post-) treatment SOI data 60. Additionally or alternatively, the SOI metadata 70 can also include changes between corresponding baseline and treatment global data 26, which can be calculated for a region or zone in which the SOI resides. In this way, the amount of change in one or more SOI characteristics (e.g., determined by the local analyzer) between baseline and post-treatment can be recorded and stored in memory as documentation.

Figure 3:
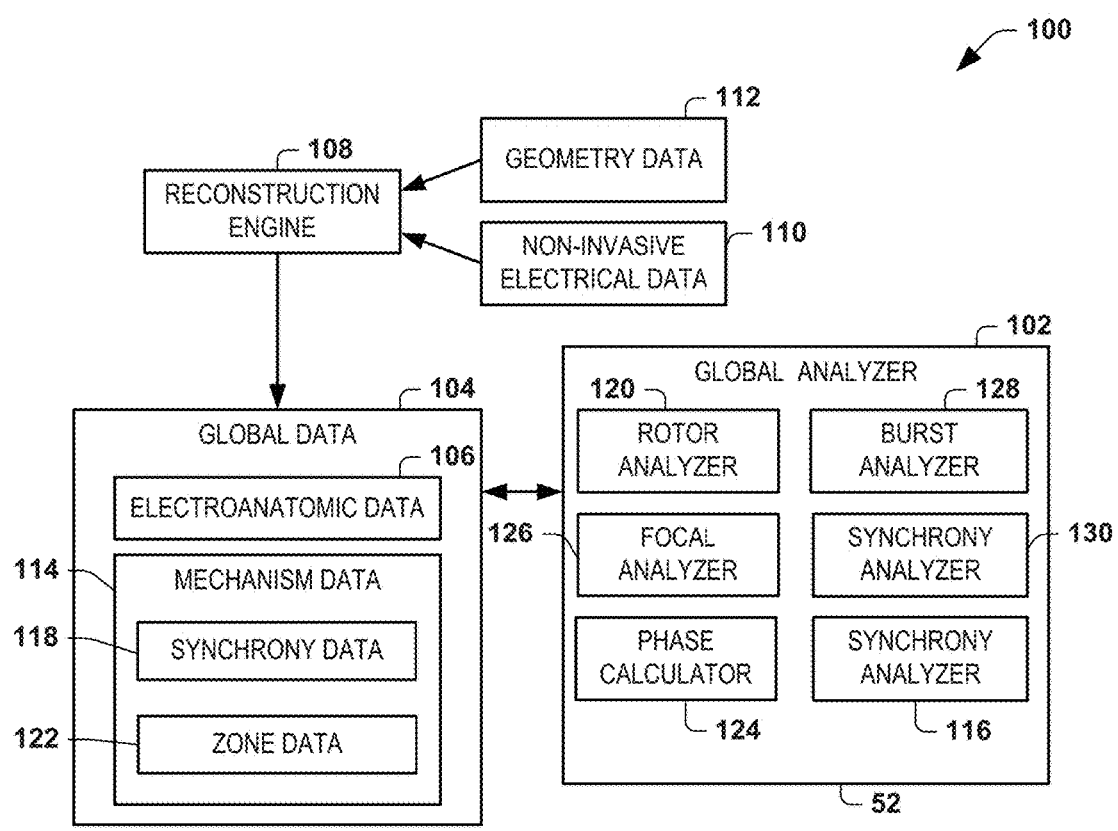
FIG. 3 depicts an example of block diagram to implement mechanism analysis.

FIG. 3 depicts another example of a global analysis subsystem 100 to process non-invasively acquired electrical data 110. A global analyzer 102 can generate global data 104 based on non-invasively acquired electrical data 110 to represent zonal or global characteristics for a region of interest of a desired anatomical structure of the patient, such as to provide a beat-by-beat information across one or more spatial zones, across multiple chambers and, in some cases, for the entire cardiac surface. The tagging system 12 (FIG. 1) can integrate the global data 104 produced by the system 100 with the SOI data 54 provided by the system 50 of FIG. 2 to facilitate understanding progress and/or to determine treatment endpoints.

In the example of FIG. 3, the system 100 can include a reconstruction engine 108 to process the non-invasive electrical data 110 in conjunction with geometry data 112 to provide corresponding non-invasive electroanatomic data 106 for a geometric surface, such as a cardiac envelope, defined by the geometry data. As used herein, an envelope can correspond to an actual anatomic surface (e.g., the epicardial surface) or a virtual surface within a patient's body that is associated with the region of interest, namely a patient's heart. The geometry data 112 can be stored in memory (e.g., memory 18) based upon information obtained via an imaging system, such as magnetic resonance imaging (MRI), computed tomography (CT), xray or other system.

For example, the geometry data 112 can include information in a three-dimensional coordinate system that represents the spatial geometry of the anatomic region of interest (e.g., a patient's heart), the spatial location of the plurality of sensors that are utilized to measure the non-invasive electrical data 110 relative to the location of the heart and the location of the body surface on which the sensors have been positioned. The reconstruction engine 108, for example, is configured to reconstruct electrical activity for a plurality of nodes spatially distributed over a cardiac envelope based on the geometry data 112 and the non-invasive electrical data 110 acquired over one or more time intervals. In some examples, the number of nodes can be greater than 1,000 or 2,000 or more depending upon the reconstruction process implemented by the reconstruction engine 108. As a further example, the non-invasive electro-anatomic data 106 can correspond to unipolar or bipolar electrograms at nodes spatially distributed over the cardiac envelope.

The global analyzer (e.g., corresponding to the analyzer 24 of FIG. 1) 102 is programmed to identify one or more global characteristics, such as an indication of synchrony or arrhythmia mechanisms, for a region or zone that contains one or more SOIs. The global analyzer 102 calculates the global characteristics based on non-invasive electrical data 110. In the example of FIG. 2, the global analyzer 102 includes a synchrony analyzer 116, a rotor analyzer 120, a phase calculator 124, a focal analyzer 126, a burst analyzer 128 and a zone identifier 130. While certain example methods are demonstrated in FIG. 2 for detecting and characterizing mechanisms of distinct arrhythmogenic electrical activity, the analyzer 102 can be extensible and user programmable to detect and identify other mechanisms and compute various indices. The analyzer generates mechanism data 114, which can include synchrony data 118 and zone data 122.

The synchrony analyzer 116 can be programmed to generate synchrony data for a region of interest based on the electroanatomic data 106 (e.g., derived from non-invasive electrical data). The synchrony analyzer 116 can compute one or more indexes (e.g., a global index, a regional index or a combination of one or more indexes) to describe an indication of synchrony (or dyssynchrony) for one or more regions on the anatomical ROI (e.g., cardiac envelope) based on non-invasive electrical data. Examples of approaches that can be utilized to compute one or more indications of synchrony are disclosed in the U.S. Patent Publication No. 2013/0245473, corresponding to U.S. patent application Ser. No. 13/882,912, which is incorporated herein by reference.

The phase calculator 124 is programmed to compute phase of the electrical signals (e.g., electrograms) that have been reconstructed onto nodes distributed over the cardiac envelope. As an example, the geometric envelope can be represented as a mesh, including a plurality of nodes interconnected by edges to define the mesh. The phase calculator 124 can be programmed to convert each cycle of electrical signal into a periodic signal as a function of time. For example, the phase calculator 124 can assign each point in time in between the beginning and end of each cycle a phase value, such as between $[-\pi$ and $\pi]$ in an increasing manner. The phase calculator 124 can compute the phase information for several time intervals at various points in time to make the analysis robust in terms of temporal and spatial consistency. In some examples, the phase calculator 124 can provide corresponding phase data for each location (e.g., about 2000 or more points) on the cardiac envelope for one or more time intervals for which the electrical data has been acquired. Since the electrical signals can be measured and/or derived concurrently for an entire geometric region (e.g., over up to the entire heart surface), the computed phase data and resulting wave front likewise are spatially and temporally consistent across the geometric region of interest. In some examples, the phase data thus can correspond to phase across the entire surface of the patient's heart. In other examples, the phase data can correspond to one or more regions of interest which can include multiple chambers of a patient's heart for the same time intervals.

An example of how the phase calculator 124 can determine phase based on electrical data 110 is disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized to determine phase, in other examples. In some examples, the non-invasive electrical data can correspond to real time data that is acquired over time. In other examples, the non-invasive electrical data that is acquired from the sensors attached to the patient's body surface prior to an EP procedure study or the like.

The rotor analyzer 120 can be programmed to analyze the phase data stored in memory to detect and characterize rotor dynamics temporally and/or spatially for the cardiac envelope. For instance, the rotor analyzer 120 can identify locations on the geometric surface corresponding to one or more rotor core trajectories based on wave front data derived from the phase data. The rotor analyzer 120 can also detect one or more stable rotor cores and derive related information for one or more of the detected stable rotors. For example, the rotor analyzer 120 can compute statistics for stable rotors across the geometric surface over time and/or ascertain connectivity between rotors.

For example, the rotor analyzer 120 can group rotors into respective zones depending on the anatomical location where such rotors are detected on the cardiac envelope. Within a zone, rotors can be counted a few different ways. As one example, summing the total number of rotations in a given zone can be summed together to provide an indication of the number of rotors. Another example to quantify rotors in a spatial zone is a sustainability index (e.g., a ratio for a region or globally) over a defined time interval (e.g., a duration selected automatically or in response to a user input) as follows:

$$\text{Rotor Sustainability} = \frac{\sum \text{rotor rotations}}{\sum \text{rotor detections}} \qquad \text{Eq. 1}$$

For instance, zone 1 has 4 detections: 1.5, 1.5, 3, and 2 rotations. Zone 2 has 2 detections: 2.5, 3. First method yields 8 rotors in Zone 1 and 5.5 rotors Zone 2. The second example method (e.g.,sustainability ratio) results in 2 (e.g., sum of all/# of detections from Eq. 1) for Zone 1, and 2.75 for Zone 2.

As a further example, the rotor analyzer 120 can compute a time-weighted average on the nodes along each trajectory and remove nodes that are further than a predetermined distance from a center (e.g., centroid) of the identified wave break point trajectory. After nodes that are further than the predetermined distance are removed, another average can be computed until all of the remaining points are within a predetermined distance (e.g., a radius) from the center of the remaining trajectory. The process can further be repeated until all of the remaining portions that are not within a predetermined distance of the center have been removed, until they are part of some sub trajectory.

As another example, the rotor analyzer 120 can implement a clustering algorithm to cluster wave break points, spatially and temporally, in a given rotor core trajectory based on the predetermined distance for clustering the rotor to determine the stable portions. Each stable rotor portion can define a respective rotor and the total number can be aggregated for a given zone (e.g., spatially and/or temporally) to provide the number of rotors that occur with such zone during the one or more time intervals. The resulting rotor information can be stored in mechanism analysis data 74, and utilized to generate a graphical visualization to present spatially and temporally consistent information in the one or more maps (e.g., presented according to a color scale or grayscale). An example of methods that can be implemented by the rotor analyzer 120 is disclosed in U.S. patent application Ser. No. 14/273,458, filed May 8, 2014, and entitled ANALYSIS AND DETECTION FOR ARRHYTHMIA DRIVERS, which is incorporated herein by reference.

The focal analyzer 126 is configured to identify one or more focal points based upon the phase data computed for the nodes in the cardiac envelope. A focal point (referred to herein in the plural as foci) corresponds to one or more origins of electrical activity, such as an arrhythmias (e.g., atrial fibrillation, atrial tachycardia, ventricular fibrillation, ventricular tachycardia or the like). A focal point can thus refer to any point a location where an activation initiates and spreads out from such initial location to its surrounding tissue. By way of example, the focal analyzer 126 can identify foci for a given geometric surface based on analysis spatial and temporal information related to activation and phase of signals for nodes across a geometrical surface. The analysis can include a comparison of a phase of node on the given geometric surface relative to the phase of nodes residing in a neighborhood (e.g., one or more layers of nodes) around the given node. The comparison can be made between the given node and its neighboring nodes over a time period sufficient to encompass a trigger event—corresponding to a focal point. For instance, neighbors of a focal point node have a later activation time, but are synchronized in phase with the focal point node. Scores can be assigned to each node based on comparisons. A corresponding focal point map can be generated based on the scores accumulated for each node. The phase data for the nodes can be provided by the phase calculator as mentioned above, and the activation times for such nodes can be determined for such nodes based on the electroanatomic data 106.

As another example, the focal analyzer 126 can identify focal points for a given geometric surface by analyzing a set of one or more focal candidate nodes according to a spread of activation from an initial focal candidate node relative to surrounding nodes in a neighborhood (e.g., one or more layers) around the initial candidate node. For instance, the focal analyzer 126 employs rules evaluate the spread of activation spatially and temporally to determine whether or not to classify the initial focal candidate node as a focal point. The resulting focal point data can also be stored in mechanism analysis data 74 and utilized to generate a graphical visualization to present spatially and temporally consistent information in the one or more maps (e.g., presented according to a color scale or grayscale).

By way of further example, from a mathematical definition, at a given time t, the focal analyzer 126 can determine that a focal point occurs at a given node x if $$\phi_x(t) > \phi_{l,i}(t), \forall l=1 \ldots n, i \in N_l(x), \quad \text{Eq. 2}$$

where: $\phi_x(t)$ is the phase value at vertex x at time t,
$\phi_{l,i}(t)$ is the phase value at the ith vertex in the lth layer of neighborhood,
n is an adjustable parameter to control number of layers, and
$N_l(x)$ is a set containing all vertices in the lth layer of neighborhood of vertex x, as demonstrated in the layered neighbor diagram of FIG. 2.

To make this process robust against noise, several layers (e.g., n=2 to n=4 or more) of neighbors around a given node can be utilized. A focal trigger typically will last at least a few milliseconds. Accordingly, the inequality above shall hold for a few consecutive samples across a time interval.

$$\phi_x(t) > \phi_{l,i}(t), \forall l=1 \ldots n, i \in N_l(x), t=1 \ldots m \quad \text{Eq. 3}$$

where m is an adjustable parameter to control the minimum duration of this event to classify a vertex to be a focal (e.g., m=5 ms).

The phase comparison based on Eq. 3 can be performed at the time of activation for node X as well as for a post activation period of time following the activation time. The time period for which the comparison is evaluated following activation at X can be a fixed default time period or it may be user programmable. In some examples, a variable evaluation time period can be set to vary based on the number of layers being evaluated in the neighborhood of node X (e.g., a greater number of layers can employ a larger time period to accommodate for spread). As an example, the activation time for each node, including the given node X, can be determined based on a time derivative of the electrogram signal at X, such as may be the time of minimum slope for the electrogram at X or maximum absolute slope; although other activation time detection algorithms may be used.

To represent the focal detection result numerically, for each node detected as a focal point per Eq. 3 above, phase comparator can score a given node with 1, for multiple instances occurring at the same or different nodes, such that the focal analyzer 126 can accumulate scores for each node. As a mathematical example, the focal point analysis module 14 can compare computed phases of neighboring signals to determine a score $F_x(t)$ for vertex x at a given sample time t, which can be represented as follows:

$$F_x(t) = \begin{cases} 1, & \text{if } \phi_x(k) > \phi_{L,i}(k), \forall l = 1 \ldots n, i \in N_l(x), k = t+1, \ldots, t+m \\ 0, & \text{otherwise} \end{cases} \quad \text{Eq. 4}$$

The focal point analysis module 14 can further calculate an aggregate score over time, such as can be represented as follows:

$$CF_x = \sum_t F_x(t) \quad \text{Eq. 5}$$

As a further example, the focal analyzer 126 can establish a variable scoring to be applied for each comparison. Thus, instead of scoring each comparison between a vertex node and a neighboring node to be 1 or 0, as mentioned above, comparisons between a vertex node and neighbors can vary as a function of distance between nodes being compared. The focal analysis can further determine other focal statistics, such as including but not limited to those disclosed in PCT Publication No. WO 2014/113555, corresponding to International application no. PCT/US2014/011825, filed Jan. 16, 2014, and entitled FOCAL POINT IDENTIFICATION AND MAPPING, which is incorporated herein by reference.

As yet another example, the focal analyzer 126 can be programmed to characterize sustainability of focal drivers at a given anatomical location on a cardiac envelope based on the electroanatomic data. For example, the focal analyzer 126 calculates the number of times (e.g., occurrences) that a focal source discharges from a given anatomical location, over a prescribed time interval (e.g., an AF interval). Therefore, over a given interval each foci location will have an associated focal discharge count. The average foci discharge count of all detected sources yields the global foci sustainability index. The average foci discharge occurrence of all detected locations, within a given anatomical region, yields the local foci sustainability index. such as follows.

$$\text{Foci Sustainability} = \frac{\sum \text{focal discharges}}{\sum \text{intervals where occurred}} \qquad \text{Eq. 6}$$

A burst analyzer 128 can be programmed to compute regions of fast cycle length (e.g., cycle length acceleration) such as to identify bursting drivers based on the non-invasive electroanatomic data 106. For example, the burst analyzer 128 can compute activation time as a function of the periodic nature of the reconstructed electrograms in the electroanatomic data 106 for nodes on the cardiac envelope. The cycle length can be detected over the duration of time between consecutive activation time occurs between each adjacent pairs of beats in the interval. The cycle length can be computed for each of the plurality of nodes for which the electrograms have been reconstructed on the cardiac envelope.

For example, the burst analyzer 128 can compute the average cycle length for the plurality of reconstructed electrograms for nodes distributed across the cardiac envelope. If the average cycle length for the nodes during a time interval is sufficiently low (e.g., below a prescribed threshold, which can be user programmable), a fast cycle length node can be identified for each such node. In other examples, the average value of cycle length for the zone can be stored in memory and utilized for comparing a relative cycle length among each of the plurality of zones that have been identified by the zone identifier 70.

Additionally, as disclosed herein, the global analyzer 102 can determine sustainability of a plurality of mechanism drivers (e.g., rotor and focal drivers focal discharge), and a total sustainability could be computed by aggregating normalized values of the indices computed for each such driver. For the example, where the mechanisms include rotor and focal drivers, the mechanism analyzer can combine the sustainability calculations of Eqs. 1 and 6 to provide an aggregate sustainability, representing the degree of driver sustainability, in an anatomical location (local) or in a larger region (global), such as follows:

$$\text{Driver Sustainability} = \Sigma(\text{Rotor Sustainability} + \text{Foci Sustainability}) \qquad \text{Eq. 7}$$

The zone identifier 130 can be programmed to identify one or more zones based on one or a combination of arrhythmia mechanisms determined by the rotor analyzer 120, focal analyzer 126 and burst analyzer 128, such as described above. In some examples, a given zone may be an identified spatial area on the cardiac envelope. In other examples, the zone can include spatial and temporal components for one or more mechanisms. As an example, the zone identifier 130 can employ a clustering algorithm to identify a spatial area across the cardiac envelope to group rotors, focal points and/or fast cycle length nodes within bounded regions that define each respective zone.

By way of example, each zones can be identified by any of following 1) user predefine regions from CT geometry, 2) mechanism overlaps grouped as 1 region until perimeter beyond a threshold X, 3) manual definition on map depending upon locations of detected mechanisms.

1) Following cardiac segmentation, user defines perimeter by drawing the zones on the cardiac envelope, each with unique anatomical name. Such drawing of the zones can be done before reconstruction, provided that cardiac mesh points are known.
2) Automatic zone definition can be determined based upon the spatial overlap of mechanisms (e.g., rotor drivers, focal point drivers or bursting drivers). A given zone would extend as far as there is overlap, until it reaches certain threshold. In this case, the automatic zone definition can split "oversize zone" in ½.
3) Post-inverse problem and rotor/foci detection, user can circle regions specific to that patient in response to a user input (e.g., via a drawing tool). Based on the encircled regions, the set of node points with in each region would be spatially registered as residing with the zones.

The global analyzer 102 thus can provide mechanism data 114, which that can include synchrony data 118 and zone data, which can be computed from non-invasive electrical data 110, such as disclosed herein. The zone data, for example, can include statistics describing an identification of the number of rotors that occur in a given zone during a given time interval, the number of focal points within a given zone during the given time interval, sustainability characteristics determined for the given zone as well as information describing cycle length acceleration for the respective zone in the given time interval. The global data 104 thus can be provided as an output (e.g., output data 14) which can be in turn rendered as part of a graphical 3D map on a display or other form of output device. The global data 104 further can be stored in memory and utilized by other systems and methods disclosed herein.

Figure 4:
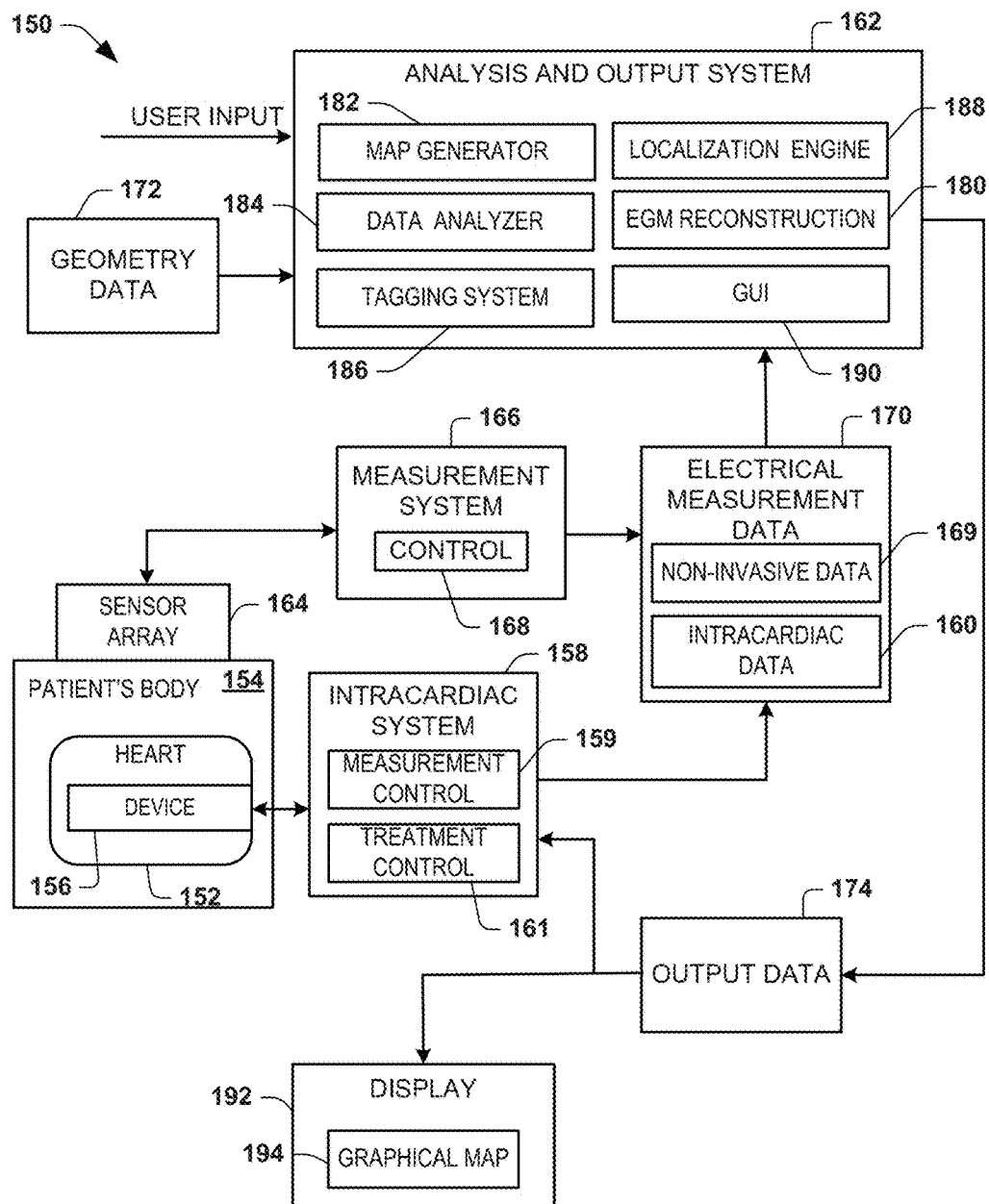
FIG. 4 depicts an example of a system that can be utilized for analysis and/or treatment of cardiac disease or disorder.

FIG. 4 depicts an example of a system 150 that can be utilized for performing diagnostics and/or treatment of a patient. In some examples, the system 150 can be implemented to generate corresponding graphical outputs for signals and/or graphical maps for a patient's heart 152 in real time as part of a diagnostic procedure (e.g., monitoring of signals during an electrophysiology study) to help assess the electrical activity for the patient's heart. Additionally or alternatively, the system 150 can be utilized as part of a treatment procedure, such as to help a physician determine parameters for delivering a therapy (e.g., delivery location, amount and type of therapy) and provide a visualization to facilitate determining when to end the procedure.

For example, an invasive device 156, such as an EP catheter, having one or more electrodes affixed thereto can be inserted into a patient's body 154. The electrode can contact or not contact the patient's heart 152, endocardially or epicardially, such as for measuring electrical activity at one or more sites. Those skilled in the art will understand and appreciate various type and configurations of devices 156, which can vary depending on the type of treatment and the procedure.

The placement of the device 156 can be guided based on position information determined via a localization engine 188, which can operate to localize the device 156. The guidance can be automated, semi-automated or be manually implemented based on information provided. The localization engine 188 can localize the device 156 and provide coordinates for the device and its electrodes. The localization engine can be implemented as part of an analysis and output system 162 or it can be a separate system that provides location data for the device and electrodes. Where a separate navigation system (e.g., a standalone system or integrated into the intracardiac system 158) is utilized to provide position data for the device 156, the navigation system can in turn provide location or position data to the analysis and output system, which can be stored in memory and co-registered with the geometry data 172 for the patient.

Examples of navigation systems commercially available include the CARTO XP EP navigation system (commercially available from Biosense-Webster) and the ENSITE NAVX visualization and navigation technology (commercially available from St. Jude Medical); although other navigations systems could be used to provide the position data for the device and associated electrodes. Another example of a navigation system that can be utilized to localize the position of the device 156 is disclosed in U.S. Provisional Patent Application No. 62/043,565, filed Aug. 29, 2014, and entitled LOCALIZATION AND TRACKING OF AN OBJECT, which is incorporated herein by reference. For example, the device 156 can include one or more electrodes disposed thereon at predetermined locations with respect to the device. Each such electrode can be positioned with respect to the heart via the device 156 and its location in a three-dimensional coordinate system can be determined by the localization engine 188 according to the type of navigation system. The sensors thus can sense electrical activity corresponding to each applied signal. The sensors can also sense other electrical signals, such as corresponding to real-time electrograms for the patient's heart.

The invasive measurement system 158 can include a measurement control 159 configured to process (electrically) and control the capture of the measured signals as to provide corresponding intracardiac data 160. The system 158 can also include a treatment control 161 to control application of treatment via the device 156, such as disclosed herein.

By way of example, the device 156 can apply the signal as to deliver a specific treatment, such as ablation, a pacing signal or to deliver another therapy (e.g., providing electrical therapy, or controlling delivery of chemical therapy, sound wave therapy, or any combination thereof). For instance, the device 156 can include one or more electrodes located at a tip of an ablation catheter, such as for applying RF energy for ablating the heart, in response to electrical signals supplied by the system 158. Other types of treatment can also be delivered via the intracardiac system 158 and the device 156 that is positioned within the body. The therapy delivery means can be on the same catheter or a different catheter probe than is used for sensing electrical activity via measurement control.

As a further example, the intracardiac system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. The treatment control 161 can control parameters of the signals supplied to the device 156 (e.g., current, voltage, repetition rate, trigger delay, sensing trigger amplitude) for delivering treatment (e.g., ablation or stimulation) via the electrode(s) on the invasive device 156 to one or more location on or inside the heart 152. The treatment control 161 can set the therapy parameters and apply electrical or other treatment based on automatic, manual (e.g., user input) or a combination of automatic and manual (e.g., semiautomatic) controls. One or more sensors (not shown but could be part of the device) can also communicate sensor information back to the system 158. The location where such therapy is applied can also be determined (e.g., by localization engine 188 or in response to a user input), such as disclosed herein.

As one example, the position of the device 156 relative to the heart 152 can be determined by the localization engine 188, which can be tracked intraoperatively via an output system 162 when implemented during a procedure. The location of the device 156 and the treatment parameters thus can be combined to help control therapy as well as to record the location where the therapy is applied. The localization can also be performed based on previously stored data separately from a procedure. Additionally, the application of therapy (e.g, manually in response to a user input or automatically provided) can cause a timestamp or other time identifier to be tagged (e.g., as metadata) to the measurement data to identify when the therapy is applied and trigger localization to identify the location where the therapy is applied via the device 156. Other metadata describing the treatment (e.g., type, delivery parameters etc.) can also be stored in memory with the measurement data.

Before, during and/or after delivering treatment (e.g., via the system 158), the non-invasive measurement system 166 and/or measurement control 159 of system 158 can be utilized to acquire electrophysiology information for the patient. The analysis and output system 162 can implement methods programmed to identify one or more zones containing arrhythmia mechanisms as well as intracardiac signal characteristics for sites within the identified zones, such as disclosed herein. In the example of FIG. 4, a sensor array 164 includes a plurality of sensors that can be utilized non-invasively for recording patient electrical activity. As one example, the sensor array 164 can correspond to a high-density arrangement of body surface sensors that are distributed over a portion of the patient's torso for measuring electrical activity associated with the patient's heart (e.g., as part of an electrocardiographic mapping procedure).

An example of a non-invasive sensor array 164 that can be used is shown and described in International Application No. PCT/US2009/063803, filed 10 Nov. 2009, which is incorporated herein by reference. Other arrangements and numbers of sensors can be used as the sensor array 164. As an example, the array can be a reduced set of sensors, which does not cover the patient's entire torso and is designed for measuring electrical activity for a particular purpose (e.g., an arrangement of electrodes specially designed for analyzing AF and/or VF) and/or for monitoring one or more predetermined spatial regions of the heart 152.

As mentioned, one or more sensor electrodes may also be located on the device 156 that is inserted into the patient's body. Such sensors can be utilized in conjunction with the non-invasive sensors in the array 164 for mapping electrical activity for an endocardial surface, such as the wall of a heart chamber, as well as for an epicardial envelope. The measurement system 166 can include appropriate controls and signal processing circuitry 168 for providing corresponding non-invasive electrical measurement data 169, which can be stored as part of the electrical measurement data 170 with the intracardiac electrical data 160. The measurement data 170 can include analog and/or digital information. The system 150 can also employ geometry data (e.g., corresponding to geometry data 58) 172 in combination with the non-invasive data 169, such as disclosed herein.

The non-invasive measurement control 168 can also be configured to control the data acquisition process (e.g., sample rate, line filtering) for measuring electrical activity and providing the non-invasive measurement data 169 for each of a plurality of locations, which are specified by the geometry data. In some examples, the control 168 can control acquisition of measurement data 170 separately from the therapy system operation, such as in response to a user input. In other examples, the measurement data 170 can be acquired concurrently with and in synchronization with delivering therapy, such as to detect electrical activity of the heart 152 that occurs in response to applying a given therapy (e.g., according to therapy parameters) or specific signals applied for purposes of localization. For instance, appropriate time stamps can be utilized for indexing the temporal relationship between the respective measurement data 160 and 169 and delivery of therapy.

The analysis and output system 162 can be programmed to implement an electrogram reconstruction engine 180 and a map generator 182 for producing electroanatomic maps. By way of example, electrogram reconstruction 180 can be programmed to compute an inverse solution and provide corresponding reconstructed electrograms (e.g., corresponding to non-invasive electroanatomic data 106) based on the non-invasive data 169 and the geometry data 172. The geometry data 172 that is utilized by the electrogram reconstruction 180 can correspond to actual patient anatomical geometry, a preprogrammed generic model or a combination thereof (e.g., a model that is modified based on patient anatomy). The reconstructed electrograms thus can correspond to electrocardiographic activity across a cardiac envelope, and can include static (three-dimensional at a given instant in time) and/or be dynamic (e.g., four-dimensional map that varies over time).

Examples of inverse algorithms that can be utilized by the reconstruction engine 180 in the system 150 include those disclosed in the U.S. Pat. Nos. 7,983,743 and 6,772,004, which are incorporated herein by reference. The reconstruction engine 180 thus can reconstruct the body surface electrical activity measured via the sensor array 164 onto a multitude of locations on a cardiac envelope (e.g., greater than 1000 locations, such as about 2000 locations or more). In other examples, the analysis and output system 162 can compute electrical activity over a sub-region of the heart based on electrical activity measured directly and invasively, such as via the device 156 (e.g., including a basket catheter or other form of measurement probe). As mentioned, the direct measurements may also constrain the computation implemented by the reconstruction 180.

As a further example, the geometry data 172 that is utilized by the reconstruction engine 180 may include a graphical representation of the patient's torso, such as image data acquired for the patient. For example, the geometry data 172 can be acquired using nearly any imaging modality (e.g., CT, MRI, ultrasound, xray or the like) based on which the corresponding representation of the cardiac envelope can be constructed, such as described herein. Such imaging may be performed concurrently with recording the electrical activity that is utilized to generate the electrical measurement data 170 or the imaging can be performed separately (e.g., before or after the measurement data has been acquired). For instance, such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements.

The geometry data 172 can further correspond to a mathematical model, such as can be a generic model or a model that has been constructed based on image data for the patient. Appropriate anatomical or other landmarks, including locations for the electrodes in the sensor array 164 can be identified in the geometry data 172 for display in conjunction with computed location information for the device. The identification of such landmarks and can be done manually (e.g., by a person via image editing software) or automatically (e.g., via image processing techniques).

The output system 162 can generate corresponding output data 174, based on the electrical measurement data (e.g., noninvasive data 169 and/or intracardiac data 160), which output data that can in turn be rendered as a corresponding graphical output in a display 192, such as including electrical activity reconstructed on the cardiac envelope or electrical characteristics derived from such reconstructed electrical activity, as mentioned above. The electrical activity or derivations thereof can be displayed on graphical model of patient anatomy or superimposed on the electrocardiographic map 194.

The output system 162 may also generate an output to identify a location of the device 156 based on coordinates determined by the localization engine 188. The output data 174 can represent or characterize the position of the device 156 in three-dimensional space based on coordinates determined according to any of the approaches herein. Additionally, the location (or a corresponding path) can be displayed at the spatial locations across a cardiac envelope (e.g., on an epicardial or endocardial surface of the heart 152). The output system 162 can display the location separately. In other examples, the location can be combined with other output data, such as to display location information on graphical map of electrical activity of the heart 152, such as a with respect to the locations of one or more zones.

Additionally, in some examples, the output data 174 can be utilized by the system 158 in connection with controlling delivery of therapy or monitoring electrical characteristics. The controls 159 and/or 161 implemented by the intracardiac system 158 can be fully automated control, semi-automated control (partially automated and responsive to a user input) or manual control based on the output data 174. In some examples, the control 160 of the therapy system can utilize the output data to control one or more therapy parameters. In other examples, an individual can view the map generated in the display to manually control the therapy system at a location determined based on this disclosure. Other types of therapy and devices can also be controlled based on the output data 174 and corresponding graphical map 194.

As disclosed herein, the analysis and output system 162 includes a data analyzer 184 such as corresponding to the data analyzer 16 of FIG. 1. Briefly stated, the data analyzer can include an SOI analyzer (e.g., analyzer 20 or 52) and a global analyzer (e.g., analyzer 24 or 102). Thus, the data analyzer 184 thus can identify and/or characterize one or more zones as well as identify one or more one or more mechanisms of distinct arrhythmogenic electrical activity. For example, the data analyzer 184 can specify the number or types of arrhythmia mechanisms that have been identified for a zone or other spatial region. The data analyzer 184 further can provide other information (e.g., statistics) computed for each respective zone based on the non-invasive data 169. Additionally or alternatively, data analyzer 184 can provide global data describing an indication of synchrony for one or more region, such as disclosed herein and in the above-incorporated U.S. Patent Publication No. 2013/0245473.

The data analyzer 184 can also analyze SOI data (e.g., corresponding to the function of SOI analyzer 20) to determine intracardiac signal characteristics (e.g., cycle length, cycle length variation, fractionation, percent of continuous activation as well as various statistics thereof determined individually or in combination) based on analysis of the intracardiac data 160. In response to updates in some or all of the electrical measurement data 170, the analysis and output system 162 thus can dynamically update the priority information, mechanism data, and intracardiac signal characteristics and generate corresponding updated output data 174.

A tagging system 186 can further generate metadata (e.g., corresponding to metadata 70) based on the electrical measurement data 170 and treatment control 161. The tagging system 186 can correspond to the tagging system 12 of FIG. 1. As disclosed herein, the intracardiac system 158 also includes treatment control 161 that can be utilized to apply treatment to a patient's body via a device 156, which can be automatic control based on the output data, semi-automatic or manual controls in response to user inputs (e.g., via GUI 190). The treatment can include, for example, ablation (e.g., RF ablation, cryoablation, surgical ablation or the like) as well as other forms of treatment disclosed herein. The electrical measurement data 170, including non-invasive data and intracardiac data, can be acquired concurrently (or separately in response to user controls). Additionally, the analysis and output system 162 can evaluate the computed data to ascertain changes in computed zone analysis, intracardiac analysis and/or priority, which changes can be provided in the output data 174 (e.g., based on comparisons by evaluator 102) to provide useful clinical data to facilitate the diagnosis and treatment process.

The tagging system 186 can implement methods programmed to analyze the input electrical measurement data 170 to determine corresponding baseline data. The baseline data can include measured signals (e.g., intracardiac signals and non-invasive signals) over respective measurement intervals as well as signal characteristics derived from such measured signals. For example, the signal characteristics can include one or more mechanisms of distinct arrhythmogenic electrical activity determined from the non-invasive data and/or SOI characteristics determined from the intracardiac data. As part of a treatment procedure, for example, the tagging system 186 can further determine one or more of the following characteristics for each signal of interest (SOI):

Elimination of electrograms from baseline as ablation is applied.

Slowing of local electrogram beyond a global rate as ablation is applied to a target site Slowing of local electrogram from a baseline as ablation is applied to a target site.

Amplitude attenuation of local electrogram from baseline as ablation is applied to a target site.

Positive impact annotation sites that meet set criteria, which can be predefined and/or be user programmable in response to a user input.

Comparing pre- and post-ablation 3D maps of amplitude of electro grams.

Comparing pre- and post-ablation 3D maps of cycle lengths of electro grams.

The results can be utilized to generate metadata that annotates or tag (e.g., intraprocedurally or post-procedural) one or more target sites in corresponding output data 174 that provides visualization about a therapy delivery procedure, such as ablation. The tagging system 186 thus can be used as part of a diagnostic and/or treatment workflow to facilitate the progress of treatment, such as including ablation based on sensed electrical activity acquired for the patient. As mentioned, in some examples, the electrical activity acquired for the patient can include non-invasive body surface measurements of body surface electrical activity. Additionally or alternatively, the electrical activity acquired for the patient can include invasive measurements of heart electrical activity, including epicardial measurements and/or endocardial measurements.

The approach disclosed herein can also be utilized in real time as electrical measurements are acquired for a given patient during the procedure. The mapping outputs can be further graphically represented as 3D maps including dynamic animated movies depicting progress of a procedure.

As a further example, the output data 174 can include one or more tags and/or annotations derived from the electrical measurement data acquired for the patient over various time intervals (e.g., during the treatment procedure). In some examples, the output data 174 can include one or more output graphical maps based on phase data computed for a geometric surface of the patient's heart 152 (e.g., such as shown in FIG. 1). As disclosed herein, the maps can be computed based on electrical data that is acquired non-invasively via sensors 164 distributed on the surface of the patient's body 154, acquired invasively via electrodes position on or within the heart or is acquired both invasively and non-invasively.

Since the measurement system 166 can measure electrical activity of a predetermined region or the entire heart concurrently (e.g., where the sensor array 164 covers the entire thorax of the patient's body 154), the resulting output data (e.g., phase characterizations, mechanisms of distinct arrhythmogenic electrical activity and/or other electrocardiographic maps) 174 thus can also represent concurrent data for the predetermined region or the entire heart in a temporally and spatially consistent manner. This can be in addition to output data 174 representing SOIs and SOI characteristics derived from the intracardiac data 160. The time interval for which the output data/maps are computed can be selected based on user input. Additionally or alternatively, the selected intervals can be synchronized with the application of therapy by the treatment control 161, an indication of which the tagging system 186 can also insert into SOI data (e.g., as metadata).

By way of further example, tagging system 186 can be programmed to compute information based on the electrical measurement data 170, which can include baseline measurements (e.g., before application of therapy) as well as measurements during application of therapy and after application of therapy. The tagging system further can leverage the information determined by the data analyzer 184, which can be programmed to compute various electrical information about one or more sites where the therapy is applied or otherwise affected by the therapy that is applied at a target site, such as disclosed herein. The tagging 186 computed electrical information can be analyzed to determine a condition or characteristic for one or more regions of the anatomic surface region that can be programmatically associated (e.g., via metadata or other data associations) with the site to provide additional information about the progress (e.g., level of success) for the delivery of therapy.

The map generator 182 can be programmed to generate one or more maps based on the computed electrical information for a given geometric surface. For example, the analysis and output system 162 can provide the output data with one or more tags or annotations indicative of the condition or characteristic determined by the tagging system 186. The output data 174 can be converted to a graphical representation for visualization on a display 192. Parameters associated with the graphical representation, corresponding to an output visualization of the computed map, such as including selecting a time interval, a type of information that is to be presented in the visualization and the like can be selected in response to a user input via a corresponding visualization GUI 190. The analysis and output system 162 thus can generate corresponding output data 174 that can in turn be rendered as a corresponding graphical output in a display 192, such as including an electrocardiographic map 194 and tags/annotations.

Additionally, the output data 174 can be utilized by the treatment control 161. The control that is implemented can be fully automated control, semi-automated control (partially automated and responsive to a user input) or manual control based on the output data 174. In some examples, the control 160 of the therapy system can utilize the output data to control one or more therapy parameters. As an example, the control 160 can control delivery of ablation therapy to a site of the heart (e.g., epicardial or endocardial wall) based tagging or annotation information that has been determined by the tagging system 186. In other examples, an individual can view the map generated in the display to manually control the therapy system based on the tagging or annotation information that is visualized. Other types of therapy and devices can also be controlled based on the output data.

Figure 5:
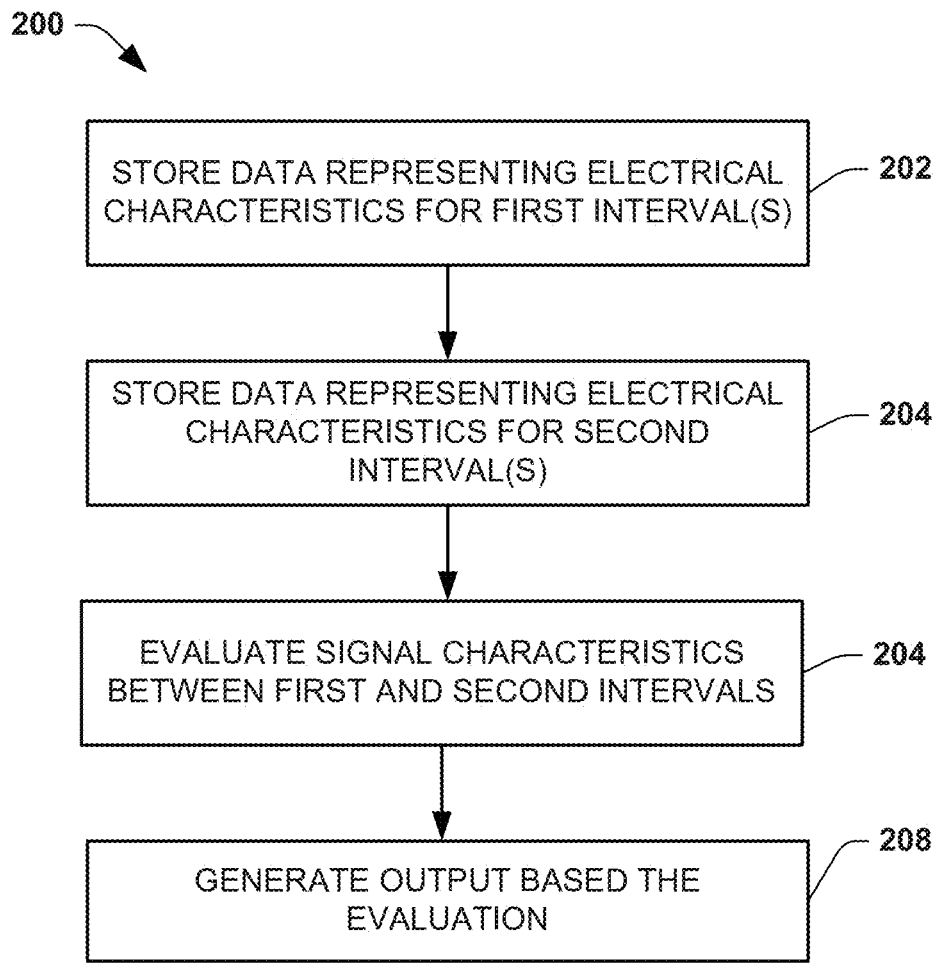
FIG. 5 is a flow diagram depicting an example of a method.

In view of the foregoing structural and functional features described above, a method 200 that can be implemented will be better appreciated with reference to flow diagram of FIG. 5. While, for purposes of simplicity of explanation, the method of FIG. 5 is shown and described as executing serially, it is to be understood and appreciated that such methods are not limited by the illustrated order, as some aspects could, in other examples, occur in different orders and/or concurrently with other aspects from that disclosed herein. Moreover, not all illustrated features may be required to implement a method. The methods or portions thereof can be implemented as instructions stored in a non-transitory machine readable medium as well as be executed by a processor of one or more computer devices, for example.

At 202, the method includes storing in memory baseline data representing at least one local or global electrical characteristics for at least a portion of a region of interest (ROI) of a patient's anatomical structure. The baseline data is determined (e.g., by data analysis 16 or 184) based on electrical measurement data obtained during at least one first measurement interval prior to applying treatment to the patient. At 204, other data is stored in memory representing the at least one local or global electrical characteristics for the at least a portion of the ROI (e.g., also determined by data analysis 16 or 184) based on electrical measurement data obtained during one or more other intervals, such as at least during and/or after applying the treatment. At 206, the baseline data is evaluated (e.g., by evaluator 30, tagging system 12 or 186) relative to the other data to determine a change in the at least one local or global electrical characteristics. At 208, an output is generated (e.g., by tagging system 12 or 186; output generator 34) based on the evaluating to provide an indication of progress or success associated with the applying the treatment. The method can be repeated during various applications of treatment to monitor and evaluate changes as to facilitate making positive changes in the electrical activity.

In some examples, the electrical characteristics are implemented as one or more mechanisms of distinct arrhythmogenic electrical activity computed based on non-invasive electrical data as disclosed herein. For instance, the mechanisms of distinct arrhythmogenic electrical activity may include one or more regional or global indication of synchrony, such as disclosed herein. Additionally or alternatively, the mechanisms of distinct arrhythmogenic electrical activity may include one or more arrhythmia mechanisms (e.g., rotor drivers, focal drivers and/or fast bursting cycle length drivers). Each of the mechanisms of distinct arrhythmogenic electrical activity being utilized can be evaluated (at 206) to determine a positive improvement in the least one of regional or global indication of synchrony based on comparing the computed characteristic(s) for the baseline interval relative to subsequent measurement intervals. Thus the method 200 provides the ability to detect positive changes in global characteristics over time (be it synchrony or other distinct arrhythmogenic mechanisms), and the ablation point that elicited that positive change can be tagged accordingly.

Figure 6:
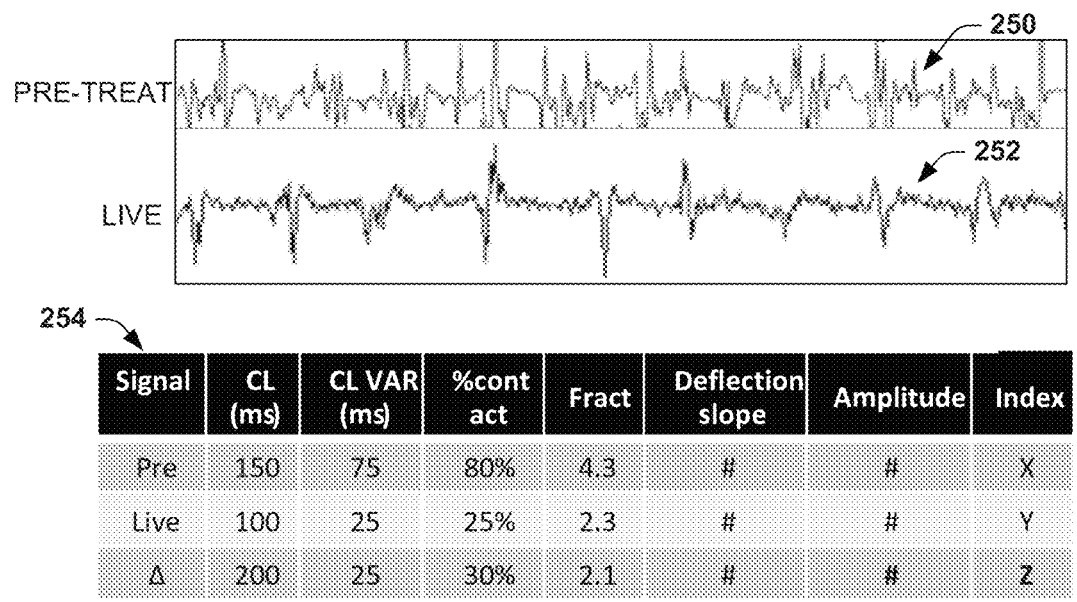
FIG. 6 depicts examples of a graphical map and corresponding electrical signals that can be generated for one or more signals of interest.

FIG. 6 depicts an example of a pre-treatment signal 250 and a live signal 252, such as can be measured directly from a patient using a measuring device, such as a catheter or other probe device. FIG. 6 also demonstrates a table 254 that includes examples of SOI characteristics that can be computed (e.g., by SOI analyzer 20 or data analyzer 184) based upon each of the signals 250 and 252. In the example of FIG. 6, the SOI characteristics include cycle length, cycle length variation, percentage of continuous activation, fractionation, deflection slope and amplitude.

Also demonstrated in FIG. 6 is a change (e.g., delta) between the pre-treatment signal and the current live signal for each of the computed SOI characteristics. The live signal characteristics and the value of change can be updated dynamically in real time based on measurements at the SOI as well as the characteristics computed for each of the pre- and live signals. The difference between the computed characteristics can also be provided in the output data (data 14) which can help guide the user to a clinical end point. The changes can be compared with respect to one or more thresholds (e.g., threshold data 32) to provide a further indication of a treatment endpoint based on comparing the change in the computed SOI characteristics relative to a corresponding threshold. As disclosed herein, different thresholds can be selected according to the global mechanisms that have been determined for a region or zone for which the SOI resides.

Figure 7:
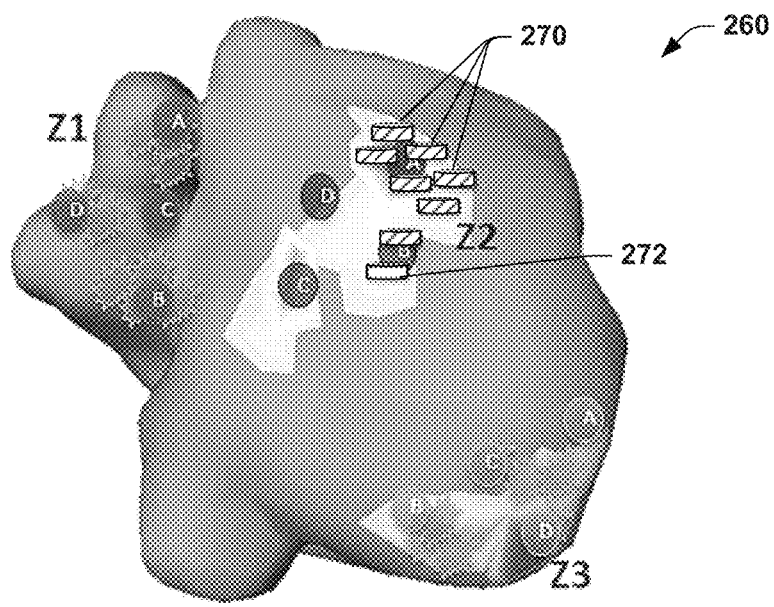
FIG. 7 depicts examples of graphical maps and corresponding electrical signals that can be generated at different phases of a treatment procedure.

FIG. 7 depicts an example of a 3-D graphical map 260 that includes a plurality of zones that include Z1, Z2 and Z3. The associated scale demonstrates examples of mechanisms of distinct arrhythmogenic electrical activity that can be identified within each of the respective zones (e.g., as determined by global analyzer 24). In the example of FIG. 7, it is assumed that treatment is being applied with respect to zone Z2. Areas where treatment has been completed is demonstrated by cylindrical discs 270 and areas where treatment is ongoing and by a disc 272 graphically differentiated from discs 270 to identify where current treatment is being applied (e.g., via an ablation catheter) or other form of treatment. Color coding, shading or other indicia can be utilized to differentiate between completed treatment sites 270 and current in-process in-treatment sites 272.

Figure 8:
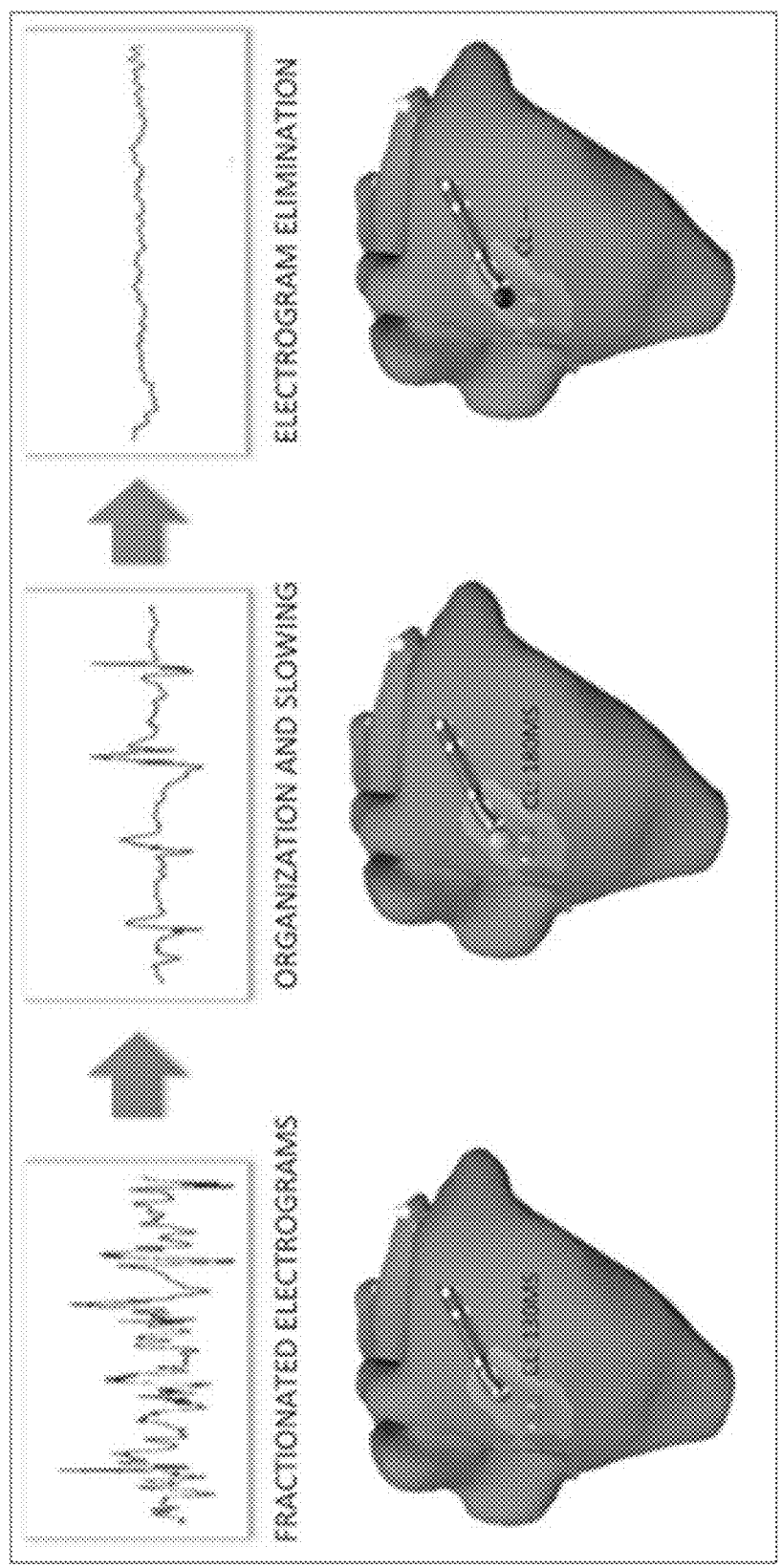
FIG. 8 depicts examples of annotation or tagging during an ablation procedure.

An example of such annotation or tagging is demonstrated in FIG. 8 during the different phases (at different times) of an ablation procedure. The visualization for each of the different phases can present a graphical depiction of a catheter superimposed an anatomical structure, such as muscle tissue (e.g., the heart or the brain) where the ablation is occurring. Different color coded indicators can also be employed to depict the progress (e.g., yellow code at a site to indicate organization and slowing and a black tag to indicate electrograms elimination (e.g, successful ablation). Cycle length (CL) can also be annotated for the corresponding target region where the ablation is being performed. For example, the region can correspond to a surface of the heart, such as can be an epicardial surface region or an endocardial surface region or a combination thereof.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A treatment method comprising:
    delivering a therapy at a given anatomic location on an anatomic region of interest;
    generating metadata associated with the delivering, the metadata identifying at least the time and the anatomic location of the therapy;
    collecting and storing in memory measurement data representative of local physiological changes resulting from the therapy based on changes in one or more measured or computed parameters; and
    displaying a graphical visualization based on the measurement data, the visualization mapping the measurement data to a graphical representation of one or more anatomic surface regions, the visualization comprising at least one annotation indicative of the metadata, to provide information about an impact of the therapy.

2. The method of claim 1, further comprising:
    generating other metadata describing the delivered therapy, the other metadata identifying one or more of the type of the therapy and delivery parameters of the therapy,
    wherein the at least one annotation is further indicative of the other metadata.

3. The method of claim 1, wherein the therapy comprises one or more of RF ablation, cryoablation, or surgical ablation of tissue.

4. The method of claim 1, wherein the therapy comprises pacing of heart tissue.

5. The method of claim 1, further comprising monitoring the local effect of the therapy based on one of interchamber synchrony, intrachamber synchrony, or arrhythmia mechanisms in a zone or region.

6. The method of claim 1, further comprising monitoring the local effect of the therapy based on global electrical characteristics combined with local signal-of-interest characteristics.

7. The method of claim 1, wherein the measurement data includes both non-invasive data acquired non-invasively and invasive data acquired invasively.

8. The method of claim 7, wherein the non-invasive data and the invasive data are acquired concurrently.

9. The method of claim 7, wherein the non-invasive data and the invasive data are acquired separately in response to user controls.

10. The method of claim 1, wherein the visualization is a dynamic animated 3D map depicting progress of the therapy.

11. The method of claim 1, further comprising analyzing the measurement data to at least one of characterize rotor activity temporally and/or spatially for the one or more anatomic surface regions or identify one or more foci for the one or more anatomic surface regions, the visualization comprising information representing results of the analyzing.

12. A treatment visualization system comprising:
a machine-readable memory;
machine-readable instructions executable by a processor, the machine-readable instructions to:
generate metadata associated with delivery of a therapy at a given memory measurement data representative of local physiological anatomic location on a region of interest (ROI) of an anatomic structure of a patient, the metadata identifying at least the time and the anatomic location of the therapy;
collect and store in the memory measurement data representative of local physiological changes resulting from the therapy based on changes in one or more measured or computed electrical parameters; and
display a graphical visualization of the measurement data mapping the measurement data to a graphical representation of one or more anatomic surface regions, the visualization comprising at least one annotation indicative of the metadata, to provide information about an impact of therapy.

13. The system of claim 12, wherein the graphical visualization is based on geometry data that is based at least in part on a preprogrammed generic model of the anatomic structure and on geometry of the patient's anatomic structure.

14. The system of claim 12, wherein the graphical visualization is based on geometry data that is based at least in part on geometry of the patient's anatomic structure.

15. The system of claim 12, wherein the machine-readable instructions further comprise instructions to generate other metadata describing the delivered therapy, the other metadata identifying one or more of the type of the therapy and delivery parameters of the therapy, and wherein the at least one annotation is further indicative of the other metadata.

16. The system of claim 12, wherein the therapy comprises one or more of RF ablation, cryoablation, or surgical ablation of tissue.

17. The system of claim 12, wherein the therapy comprises pacing of heart tissue.

18. The system of claim 12, wherein the machine-readable instructions further comprise instructions to analyze data indicative of one of interchamber synchrony, intrachamber synchrony, or arrhythmia mechanisms in a zone or region, the data including reconstructed electrograms computed for a cardiac envelope, and to monitor the local effect of the therapy based on the data.

19. The method of claim 12, wherein the machine-readable instructions further comprise instructions to analyze the measurement data to at least one of characterize rotor activity temporally and/or spatially for the one or more anatomic surface regions or identify one or more foci for the one or more anatomic surface regions, the visualization comprising information representing results of the analyzing.

20. A cardiac treatment visualization system comprising:
a machine-readable memory storing geometry data indicative of the geometry of a cardiac structure of a patient;
an input to receive position data indicative of the spatial location of an intracardiac therapy device with respect to the cardiac structure;
machine-readable instructions executable by a processor, the machine-readable instructions to:
generate metadata associated with delivery of an intracardiac therapy at a given anatomic location on a region of interest (ROI) of the cardiac structure, the metadata identifying at least the time and the anatomic location of the therapy;
collect and store in the memory measurement data representative of local physiological changes resulting from the therapy based on changes in one or more measured or computed electrical parameters; and
display a graphical visualization of the measurement data mapping the measurement data to a real-time 3D graphical representation of one or more anatomic surface regions based at least in part on the geometry data, the visualization comprising at least one annotation to the real-time 3D graphical representation indicative of the metadata, to provide information about an impact of the therapy.

* * * * *